(12) United States Patent
Hearn

(10) Patent No.: US 10,441,734 B2
(45) Date of Patent: Oct. 15, 2019

(54) INHALER

(71) Applicant: Kind Consumer Limited, London (GB)

(72) Inventor: Alex Hearn, London (GB)

(73) Assignee: KIND CONSUMER LIMITED, London (GB)

( * ) Notice: Subject to any disclaimer, the term of this patent is extended or adjusted under 35 U.S.C. 154(b) by 1041 days.

(21) Appl. No.: 14/423,799

(22) PCT Filed: Aug. 27, 2013

(86) PCT No.: PCT/GB2013/052240
§ 371 (c)(1),
(2) Date: Feb. 25, 2015

(87) PCT Pub. No.: WO2014/033439
PCT Pub. Date: Mar. 6, 2014

(65) Prior Publication Data
US 2015/0297844 A1 Oct. 22, 2015

(30) Foreign Application Priority Data
Aug. 28, 2012 (GB) .................................. 1215282.3

(51) Int. Cl.
*A61M 15/06* (2006.01)
*A24F 47/00* (2006.01)
(Continued)

(52) U.S. Cl.
CPC ........... *A61M 15/06* (2013.01); *A24F 47/002* (2013.01); *A61M 11/001* (2014.02);
(Continued)

(58) Field of Classification Search
CPC ...... A61M 15/00; A61M 15/0001–001; A61M 15/0013–0026; A61M 15/0028–0038;
(Continued)

(56) References Cited

U.S. PATENT DOCUMENTS 3,155,573 A * 11/1964 Fowler ................ A61K 9/0075
128/200.22
4,393,884 A 7/1983 Jacobs
(Continued)

FOREIGN PATENT DOCUMENTS

EP 0911048 A2 4/1999
EP 2319334 A1 5/2011
(Continued)

OTHER PUBLICATIONS

International Search Report and Written Opinion dated May 8, 2014 for Application No. PCT/GB2013/052231.
(Continued)

*Primary Examiner* — Peter S Vasat
*Assistant Examiner* — Ned T Heffner
(74) *Attorney, Agent, or Firm* — Patterson + Sheridan, LLP

(57) ABSTRACT

An inhaler comprising a source of inhalable composition. An outlet flow path is provided for the composition from the source to a composition outlet at an outlet end of the inhaler. Means are provided to generate a flow of composition from the source along the outlet flow path and out of the composition outlet when suction is applied to the outlet end. A pair of air outlets at the outlet end are arranged on opposite sides of the composition outlet through which air is drawn in respective air jets when suction is applied to the outlet end. The composition and air outlets are arranged such that, in use, the pair of air jets impinge on the composition plume.

**20 Claims, 5

(51) Int. Cl.
*A61M 15/00* (2006.01)
*A61M 11/00* (2006.01)

(52) U.S. Cl.
CPC ........ *A61M 11/002* (2014.02); *A61M 15/002* (2014.02); *A61M 15/009* (2013.01); *A61M 15/0021* (2014.02); *A61M 15/0093* (2014.02); *A61M 2206/10* (2013.01); *A61M 2209/02* (2013.01); *A61M 2209/045* (2013.01)

(58) Field of Classification Search
CPC ... A61M 15/004–0043; A61M 15/0045–0051; A61M 15/0056; A61M 15/006; A61M 15/0065; A61M 15/0068–0083; A61M 15/0086–0088; A61M 15/0091–0098; A61M 15/06; A61M 15/08–085; A24F 47/00; A24F 47/002; A24F 47/004; A24F 47/008; A61K 8/97
See application file for complete search history.

(56) References Cited

U.S. PATENT DOCUMENTS

| | | | | |
|---|---|---|---|---|
| 5,388,572 | A * | 2/1995 | Mulhauser | A61M 15/0045 128/203.15 |
| 6,413,496 | B1 | 7/2002 | Goodman et al. | |
| 2002/0144680 | A1* | 10/2002 | Nilsson | A61M 15/0045 128/203.15 |
| 2003/0235538 | A1* | 12/2003 | Zierenberg | A61K 9/0075 424/46 |
| 2004/0002520 | A1 | 1/2004 | Soderlund et al. | |
| 2010/0000529 | A1* | 1/2010 | Prime | A61M 15/0045 128/203.15 |
| 2010/0236562 | A1 | 9/2010 | Hearn et al. | |
| 2012/0085344 | A1* | 4/2012 | Luber | A61M 15/0085 128/200.16 |
| 2012/0090628 | A1 | 4/2012 | Turner et al. | |

FOREIGN PATENT DOCUMENTS

| | | |
|---|---|---|
| GB | 1017032 | 1/1966 |
| WO | 99/20331 A1 | 4/1999 |
| WO | 03/101454 | 12/2003 |
| WO | 2009090084 A1 | 7/2009 |
| WO | 2009/135729 | 11/2009 |
| WO | 2011015825 A1 | 2/2011 |
| WO | 2011107737 | 9/2011 |

OTHER PUBLICATIONS

United Kingdom Search Report dated Dec. 27, 2012 for Application No. GB1215273.2.
International Search Report and Written Opinion dated Nov. 28, 2013 for Application No. PCT/GB2013/052240.
United Kingdom Search Report dated Dec. 5, 2012 for Application No. GB1215282.3.

* cited by examiner

INHALER

The present invention relates to an inhaler. More specifically, the invention is directed to an inhaler for a simulated cigarette, namely an inhaler which has the general size and shape of a cigarette. However, the invention is also applicable to other types of inhalers, such as those for dispensing asthma medication or other forms of medication.

Many such inhalers are known. In general, the inhaler has a single orifice at the outlet end which is placed in the mouth of the user. The user then sucks on the outlet end to trigger the flow of composition into their mouth. At the same time, air is drawn through the outlet orifice into the user's mouth.

One such example is WO2006/079751 which discloses a trigger mechanism that releases medications for inhalation which can deliver liquid formulation in a bolus, such that it is necessary to deliver the whole dose of the reservoir to the user with a high output of emitted formulation that will empty the majority of the reservoir.

Some examples have looked at using the turbulent flow to accelerate particles into the inspiratory cycle. U.S. Pat. No. 6,234,169, for example, requires a conduit between a reservoir and an outlet end and an orifice in the reservoir chamber which uses the Coanda effect such that air entering via the orifice travels to the reservoir to draw medicament from the reservoir.

Further examples have looked at varying the performance of the device but changing characteristics of its mechanism to influence resistance of the device to the breath of the user. For example, WO 2008/151796 is directed to an aerosol inhaler having a mouthpiece and an air supply opening, that triggers a reservoir for a fluid to flow. This inhaler has a flow resistance of at least 60000 $Pa^{1/2}$ $s/m^3$. This is achieved through an insert in the mouthpiece in order to define or increase the flow resistance and/or to guide an airflow of air entering through the at least one air supply opening. Contrary to the present invention, the main aspect is to increase the flow resistance of the device so that the flow resistance of at least 60000 $Pa^{1/2}$ s/m3. This is significantly higher in terms of draw resistance than previous inhalers of similar the present type. Such an inhaler is considered a development in traditional metered dose actuated inhalers since a device that delivers a higher resistance than normal, will deliver a rapid bolus of formulation at a user high inhalation rate, accelerating the emitted flow into the deep lung as the inspiration is performed.

For a simulated cigarette device, it is necessary to have very different characteristics in inhalation rate. Specifically the duration of flow, rather than an emitted bolus, should aim to be as smooth and gradual as possible. For a pressurised metered dose inhaler (pMDI) inhaler, inspiration levels can be as high as 60 l/m, however for simulated cigarette devices this is required to be closer to 1-2 l/m.

In the field of simulated cigarettes, there are a number of devices currently on the market. One such device is the Nicorette® inhalator. This is provided with a cartridge containing nicotine which is placed in a housing. The user then sucks on one end of the housing thereby drawing air in through the opposite end creating a through flow of air which entrains the nicotine which is then inhaled. Thus, air and the nicotine containing composition are inhaled through a single orifice.

The second type of device is the E-cigarette. In this case, sucking on the outlet end of the E-cigarette lowers the internal pressure which triggers the operation of a heater to vaporise nicotine into the air stream such that it is inhaled at the outlet end.

A variety of other simulated cigarettes are known in the art previously yet none have addressed the tuning of devices to the desired characteristics.

For example, U.S. Pat. No. 4,635,651 discloses a self-propelled cigarette substitute but does not take into consideration the precise mechanics of inhalation cues.

DE 4030257 discloses a simulated cigarette for dispensing nicotine with a breath-activated valve. In this case a circular disc is connected via an axial rod to the outlet valve for the source of materials to be inhaled. When the user inhales, air is drawn into the device through the holes upstream of the plate and is sucked around the edge of the plate. However there is no reference to how the pressure drop and draw resistance would be controlled.

FR2873584 also provides a device which includes a pressurised formulation a space and a discharge nozzle which aims to deliver particles at sub 2 microns. However there is no consideration of the discharge mechanics suited and tunable to the users inhalation.

A recent design of simulated cigarette is disclosed in our own earlier International application WO 2011/015826. A similar device is disclosed in WO 2011/015825 and WO 2011/107737. This document discloses a simulated cigarette which has a pressurised reservoir, the outlet to which is closed by a deformable tube which is pinched by a valve member. The valve member is part of a vane supported on a membrane. When a user sucks on the outlet end of the cigarette, air is sucked out of the chamber above the membrane at a rate which is faster than the rate at which at which it enters via a number of smaller inlet orifices such that the pressure above the membrane is reduced and the valve is lifted. At the outlet end of the device, the inhalable composition leaves along a composition flow path below the membrane and there is a separate air stream from the chamber above the membrane. The nature of the valve design means that the flow paths must, of necessity, maintain this positional relationship with one orifice above the other.

One important factor in the delivery of compositions from an inhaler is to ensure that the inspiration mechanics of the user closely resemble traditional smoking inhalation for it to be an effective substitute. This means the pressure drop and draw resistance should be engineered to optimise performance. Another factor is that the particle size of the delivered composition can be relatively small, well defined and easily able to be controlled to ensure that the particle size of the composition that is delivered is at the optimal size for absorption at the desired delivery site, whether it be the (buccal cavity, lungs, etc.) and in the desired concentration.

The present invention aims to provide an inhaler with enhanced composition delivery.

According to the present invention, there is provided an inhaler comprising a source of inhalable composition, an outlet flow path for the composition from the source to a composition outlet, at an outlet end of the inhaler, means to generate a flow of composition from the source along the outlet flow path and out of the composition outlet when suction is applied to the outlet end; and a pair of air outlets at the outlet end arranged on opposite sides of the composition outlet through which air is drawn in respective air jets when suction is applied to the outlet end, the composition and air outlets being arranged such that, in use, the pair of air jets impinge on the composition plume.

The air jets create turbulence within the composition plume, thereby breaking up any larger particles of composition within the plume. As a result of this, a more uniform and generally smaller particle size is obtained. Further, the present invention allows a simple way of adjusting the particle size which may be done simply by changing the relative size and spacing of the three outlets. The present invention thus provides an inhaler which can mimic the pressure drop, draw resistance and optimised droplet sizing for a simulated cigarette device to enhance sensory performance and increase pharmacokinetic effect.

The invention therefore provides significant advantages over the device disclosed in WO 2011/015826 which does not address the issue of controlling the particle size and breath-operated performance as the arrangement of the outlet orifices is dictated by the manner in which the valve operates.

Further, the provision of a pair of air outlets provides a benefit over the single air outlet of WO 2011/015826 in which the presence of an air outlet on only one side of the composition outlet causes deflection of the composition plume. This deflection will vary depending on the amount of suction applied such that an accurate delivery of plume becomes difficult. Having an air jet on either side of the composition plume ensures that the forces exerted on the plume by the air jets are balanced thereby ensuring that the positive effects of breaking up the composition are obtained without the unwanted deflection of the plume.

Although it is preferred to have only two air outlets, it is also possible to have additional outlets. Such additional outlets could be provided singularly as, with three or more outlets, the ability of one outlet to create significant deflection of the plume is greatly reduced. However, preferably, if additional air outlets are present, they are present in at least one additional opposed pair.

If the air from the air outlets exits the inhaler in a direction parallel to the direction of the plume, there will be some degree of interference in the air jet and composition plume as these diverge away from the inhaler. However, preferably, the air outlets are angled towards the composition outlet such that the air jets converge towards the composition plume. This enhances the ability of the air jets to break up the larger particles within the composition plume. Also, it provides a further degree of "tuning" of the device in that the angle can be adjusted to retain the desired size of the particles in the composition outlet.

The means to generate the flow of the composition from the source along the outlet flow path and out of the composition outlet as a composition plume when suction is applied may take a number of forms. For example, the composition could be exposed to an air flow path through the cigarette such that, upon suction of the end of the cigarette, the through flow of air entrains some of the composition. Alternatively, there may be a battery operated heater within the cigarette which is triggered when suction is applied to vaporise an amount of nicotine. However, preferably, the source of inhalable composition is a pressurised reservoir and the means to generate a flow of the composition is a breath operated valve. In this case, the pair of air outlets may be associated with air flow passages which are independent of the actuated mechanism. However, preferably, the pair of air outlets are associated with air flow paths which at least partially operate the breath operated valve.

Making the air outlets part of the actuation mechanism of a breath operated valve provides further possibilities for tuning the simulated cigarette. By changing the sizes of the air outlets, the pressure differential applied to the breath operated valve can be varied. Thus, the suction force required to operate the breath activated valve can be tuned simply by changing the size of the air outlets.

A further benefit of having a breath operated valve which is opened at least in part by flow through a pair of air outlets which are separate from the outlet flow path for the composition is that the rate of the composition dispensed (essentially determined by reservoir pressure and minimum composition outlet area) is independent of the air flow through the air outlets. This allows the suction pressure at which the valve is triggered and the draw resistance to be set (by varying the air outlet size) independently of the amount of the composition which is dispensed. This allows the air outlet orifices to remain relatively small to provide the required pressure drop and draw resistance. However, it also allows a relatively large composition outlet which is ideal for producing the required amount of composition. Thus, the compromises of the prior art with a single orifice are avoided.

Preferably, the breath operated valve comprises a valve element biased by a biasing force into a position in which it closes the outlet flow path for the composition; a flexible diaphragm arranged to move the valve element; a first flow path partly defined by one side of the diaphragm and a second air flow path partly defined by the opposite side of the diaphragm, each flow path having an opening at the outlet end, wherein the air flow paths are arranged such that suction at the outlet end causes a reduction pressure in the first air flow path and a relative increase in pressure in the second air flow path, creating a pressure differential across the diaphragm that moves the diaphragm and hence moves the valve element against the biasing force to open the outlet flow path for the composition, wherein the pair of air outlets provide the opening at the outlet end of the second air flow path.

The air outlets may simply lead from closed chambers within the inhaler. However, preferably, the air outlets are associated with one or more air inlets spaced from the outlet end such that there is a through flow path from the air inlets to the air outlets. By varying the size of the air inlets and outlets, the draw resistance experienced by the user can be varied.

While the inhaler has been specifically designed to be a simulated cigarette, it has broader applications as an inhaler, for example, to dispense medicament, particularly in a situation where a low trigger force is required. This is especially advantageous when delivering medications or vaccines which require rapid delivery and compliance compared with traditional inhalers, for example β2-adrenergic agonists, classes of opioids including synthetic and semi-synthetic, hormones or neuro-transmitters and not limited to anticholinergics, corticosteroids, cannabinoids, PDE4-inhibitors, LTD4-antagonists, EGFR-inhibitors, dopamine agonists, antihistamines, PAF-antagonists and PI3-kinase inhibitors or LTD4-antagonists antivirals, antibiotics, antigens or therapeutic proteins.

An example of an inhaler in accordance with the present invention will now be described with reference to the accompanying drawings, in which.

The present invention relates to an improvement of the outlet valve for an inhaler such as that disclosed in WO 2011/015826. For further details of the device and its refill mechanism, reference is made to WO 2009/001078.

Figure 1:
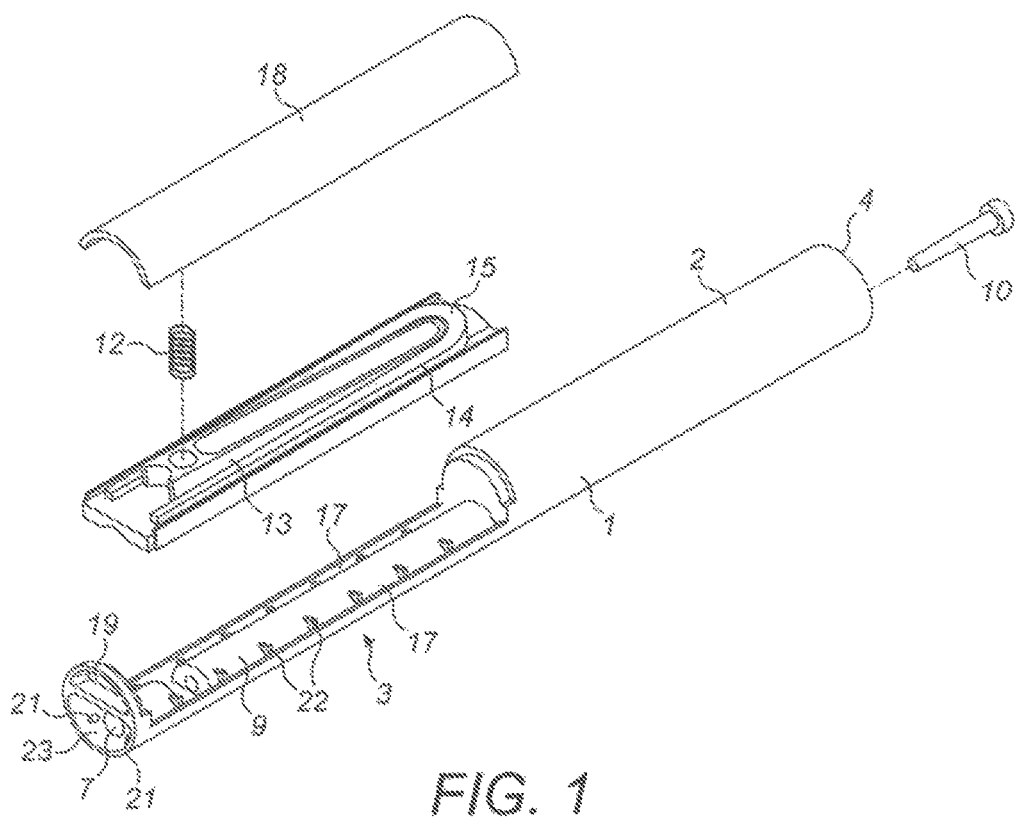
FIG. 1 is an exploded perspective view of an inhaler.

As shown in FIG. 1, the device comprises a housing 1 which is broadly divided into two parts. The distal part is a reservoir 2 and the proximal part is the breath-activated valve mechanism 3. At the distal end 4 is a refill valve 5 allowing the reservoir to be filled. The reservoir may contain a wick 6 as disclosed in PCT/GB2011/000285. At the opposite end is the outlet end 5 which will be described in more detail below.

Figure 6:
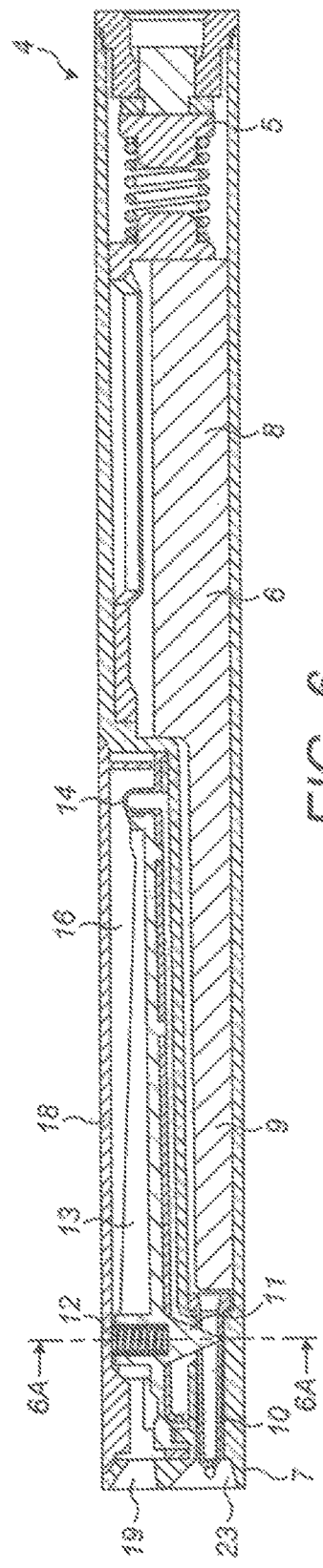
FIG. 6 is a full cross-section of the inhaler.
Figure 6A:
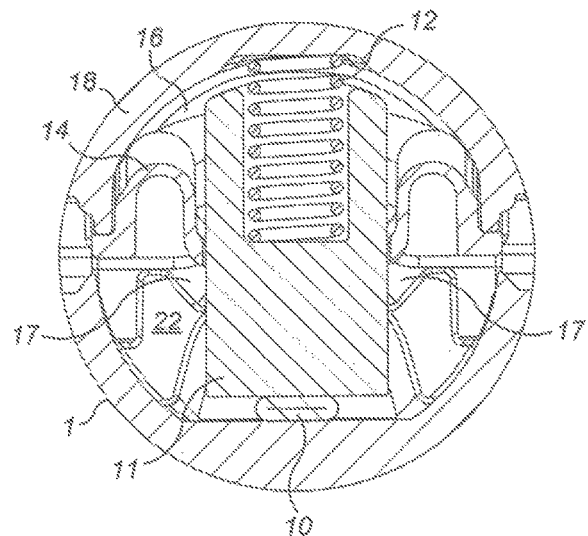
FIG. 6A is a cross-section through line 6A-6A in FIG. 6.
Figure 7:
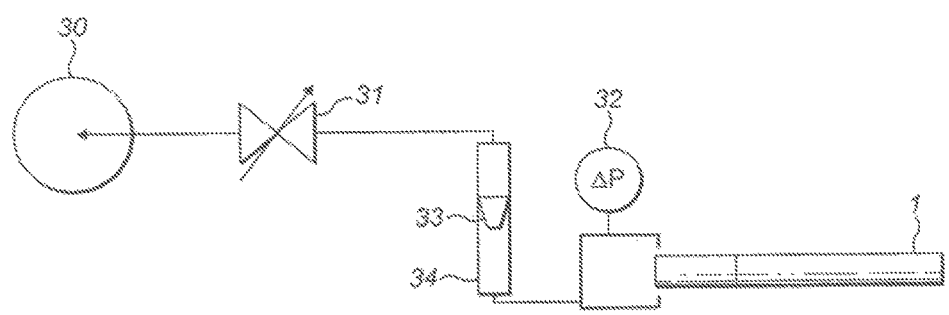
FIG. 7 is a Flow Rate Test Rig Schematic.

As best shown in FIG. 6, the reservoir has a portion 8 adjacent to the distal end 4 which occupies substantially the entire cross-section of the inhaler at this point. A second portion 9 which is closer to the outlet end 7 occupies a relatively small portion of the cross-section of the inhaler because, as shown in FIG. 6, this part of the inhaler also accommodates the valve mechanism described below and provides space for the air flow paths also described below.

Figure 3:
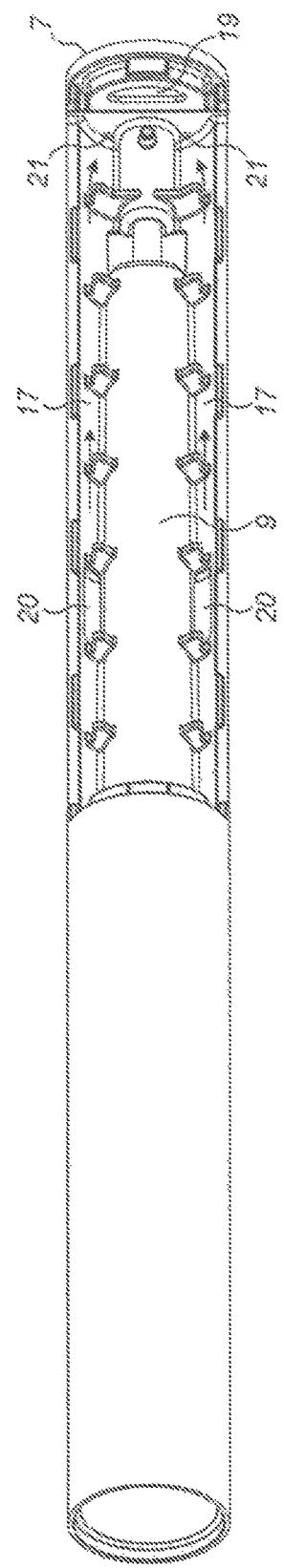
FIG. 3 is a perspective view of the outlet end of the inhaler with the cover, vane and diaphragm removed to show the air flow paths.
Figure 5:
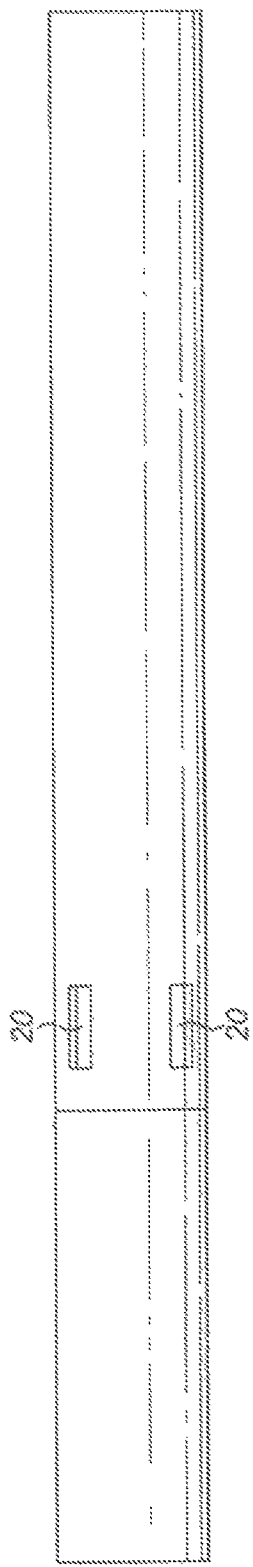
FIG. 5 is a plan view of the inhaler.

As can be seen from FIGS. 1 and 3, this second portion 9 of the reservoir is part of the same molding as the housing 1 and runs along the lower part of the inhaler.

An elastomeric insert 10 in the form of a tube open at both ends is inserted from the distal end, but forms an outlet flow path at the proximal end of the inlet path as shown in FIG. 6. This insert 10 is normally pinched closed by a valve element 11 which is biased downwardly by a spring 11. This pinch closed valve mechanism is described in greater detail in WO 2011/315825.

The valve element 11 is part of a vane 13 which extends along most of the outlet end of the inhaler. The vane 13 is surrounded by a diaphragm 14 which extends across the entire lower face of the vane 13, with the exception of the orifice through which the valve element 11 projects. This valve element is sealed around its periphery to the surrounding housing. At the distal end of the diaphragm 14 is a kink 15 which provides some degree of freedom for the vane 13 to move up and down. The vane and its frame are both made of a rigid plastic material while the diaphragm is a clearer flexible material. There is a direct connection between the material of the tongue and the material of the frame such that it is the material of the tongue which is acting as the hinge, rather than the material of the membrane. The opposite end of the vane 13 is integral with a surrounding frame that is filled into the housing such that there is a direct connection between the frame and vane to provide a hinge about which the vane pivots.

A mechanism for opening the valve element 11 against the action of the spring 12 will now be described.

This is achieved by first 16 and second 17 air flow paths. The first flow path 16 is above the diaphragm 14 with the top of the flow path being formed by housing part 18 which is fixed to the housing 1 once the valve elements are in place. The first air flow path is essentially provided by a first air flow path outlet orifice 19 which leads into the space occupied by the vane 13 above the diaphragm 14. This flow path has no other orifices.

Figure 2:
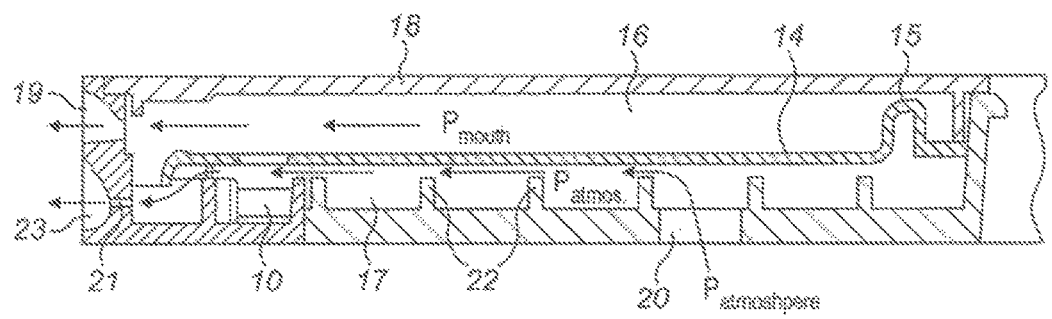
FIG. 2 is a schematic axial cross-section through the outlet end of the inhaler in the plane containing an air flow path and with the vane removed for clarity.

The second air flow path 17 is below the diaphragm 14 and is defined by a pair of second air flow path inlet orifices 20 (only one of which is shown in FIG. 2). In the present example, the second air flow path is actually defined by two separate paths which extend from the inlet orifices 20 along passages 17 which are defined by the housing 1 on the lower surface and the diaphragm 11 at its upper surface and which extends alongside the second portion 9 of the reservoir to the outlet end terminating at a pair of second air flow path outlet orifices 21 which are smaller than the corresponding inlet orifices 20. The flow through the second air flow path is depicted by arrows in the lower part of FIG. 2 and in FIG. 3. Baffles 22 are provided along the second air flow path 17 to increase the follow resistance in this path.

As a user sucks on the outlet end 7, air is sucked out of the first flow path outlet orifice 15 thereby lowering the pressure in the first air flow path 16. At the same time, air is drawn in through the second flow path air inlet orifices 20. The combination of a reduced pressure above the vane and the prevention of the significant pressure reduction below the vane causes the vane to be moved upwardly deforming the diaphragm and raising the valve element against the action of the spring 12. When a user stops sucking on the outlet end, the pressure above and below the diaphragm equalises and the spring 12 returns the valve element 11 to a position in which it pinches the insert 10 closed.

Figure 4:
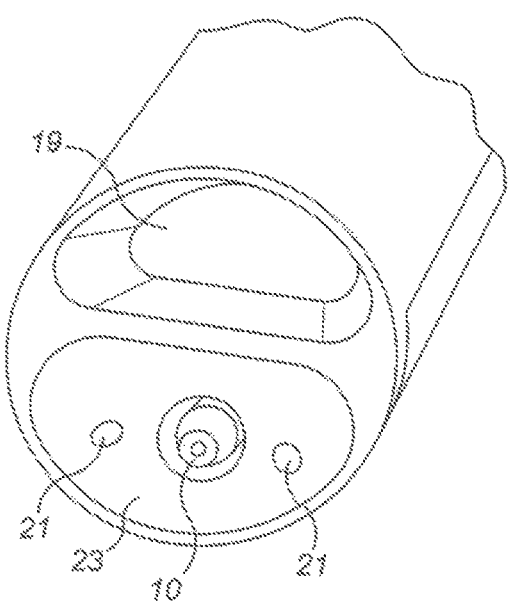
FIG. 4 is a perspective view of the outlet end of the inhaler.

As shown in FIGS. 1, 2 and 4, the outlet end 7 at the part containing the insert 10 and the air flow path outlet orifices 21 has a concave configuration 23. As a result of this, the outlet orifices 21 are inclined towards the insert 10. Upon inhalation, the air exiting the outlet orifices 21 is angled towards the plume of composition emerging from the insert 10 such that the air quickly impinges on the composition thereby creating greater turbulence and reducing the mean particle size of the composition.

For traditional tobacco cigarettes, international standards ISO:6565 and ISO 7210 govern the test and methodologies of draw resistance and pressure drop of tobacco cigarettes. This is an important measure for product quality specifications and for matching analytical determinations by mechanical smoking.

FIG. 7 is a general schematic for a test method under these standards and shows a flow rate test rig which enables an assessment of the pressure drop across the inhaler device at different flow rates. The pressure drop is applied using a vacuum pump 30 under the control of a variable restrictor 31 and is measured using a suitable pressure gauge 32, zeroing the pressure gauge before testing to compensate for changes in atmospheric pressure. The flow rate is measured from the top of a float 33 in a flow tube 34. Each inhalation is measured in accordance with ISO 7210:1997.

The size of the air jets influences the draw resistance of the inhalation such that there has found to be a direct correlation with the measured pressure drop across the air outlet orifices under ISO:7210 against the diameter of the second air flow path outlet orifices. For example, with two air such orifices each having a diameter of 0.45 mm, the mean draw resistance tested across 100 devices is 2.8 kPa. When the orifices have a diameter of 0.40 mm they give a mean pressure drop at 3.7 kPa, and when they have a diameter of 0.33 mm they give a mean pressure drop of 5.2 kPa. It is preferable for the invention that a mean pressure drop is in the range between 2 kpa and 4 kpa for the optimum performance characteristics for a smoker on an aerosolised simulated cigarette. This allows a selected tuning of the device to fit particular strength of formulation, for example a higher resistance device will be tailored for a higher strength formulation.

Our co-pending application GB 1215273.2 discloses suitable formulations for the composition. A higher draw resistance device with twin air jets of 0.38 mm in diameter can be paired with a higher strength nicotine formulation for example 0.084 w/w %. This is similar to conventional tobacco cigarettes since higher nicotine content cigarettes correlate with having higher draw resistances. Thus the inhaler can provide a method and a mechanism to tune the pressure drop across the air jet to particular strengths of formulation to deliver expanded product ranges and enhanced consumer acceptance.

The invention claimed is:

1. An inhaler comprising:

a source of inhalable composition;

an outlet flow path for the composition from the source to a composition outlet, at an outlet end of the inhaler, means to generate a flow of composition from the source along the outlet flow path and out of the composition outlet when suction is applied to the outlet end; and a pair of air outlets at the outlet end arranged on opposite sides of the composition outlet through which air is drawn in respective air jets when suction is applied to the outlet end, the composition and air outlets being arranged such that, in use, the pair of air jets impinge on the composition plume, wherein the composition outlet and the air outlet being arranged such that the inhalable composition and the air leave the inhaler separately.

2. An inhaler according to claim 1, wherein there are only two air outlets.

3. An inhaler according to claim 1, wherein additional outlets are present in at least one additional opposed pair.

4. An inhaler according to claim 1, wherein the air outlets are angled towards the composition outlet such that the air jets converge towards the composition plume.

5. An inhaler according to claim 1, where the pressure drop across the air outlets as measured with air outlets of 1 mm diameter is 3 kPa-4 kPa.

6. An inhaler according to claim 1, wherein the source of inhalable composition is a pressurised reservoir, and means to generate the flow of the composition is a breath operated valve.

7. An inhaler according to claim 6, wherein the air outlets are associated with one or more air inlets spaced from the outlet end such that there is a through flow path from the air inlets to the air outlets.

8. An inhaler according to claim 6, wherein the pair of air outlets are associated with air flow paths which at least partially operate the breath operated valve.

9. An inhaler according to claim 8, wherein the breath operated valve comprises:

a valve element biased by a biasing force into a position in which it closes the outlet flow path for the composition;

a flexible diaphragm arranged to move the valve element;

a first flow path partly defined by one side of the diaphragm; and a second air flow path partly defined by the opposite side of the diaphragm, each flow path having an opening at the outlet end, wherein the air flow paths are arranged such that suction at the outlet end causes a reduction pressure in the first air flow path and a relative increase in pressure in the second air flow path, creating a pressure differential across the diaphragm that moves the diaphragm and hence moves the valve element against the biasing force to open the outlet flow path for the composition, wherein the pair of air outlets provide the opening at the outlet end of the second air flow path.

10. An inhaler according to claim 1, where upon a standard inhalation, the flow through all of the air outlets in total is 0.5 l/m to 60 l/m.

11. The inhaler according to claim 10, where upon a standard inhalation, the flow through all of the air outlets in total is 1.0 l/m to 5 l/m.

12. The inhaler according to claim 10, where upon a standard inhalation, the flow through all of the air outlets in total is 1.5 l/m.

13. An inhaler according to claim 1, wherein the diameter of an exit of the composition outlet is 0.1 mm to 1 mm and the diameter of each of the pair of outlets is 0.1 mm to 1.2 mm.

14. The inhaler according to claim 13, wherein the diameter of the exit of the composition outlet is 0.2 mm and the diameter of each of the pair of air outlets is 0.4 mm.

15. An inhaler according to claim 1, wherein the ratio of cross-sectional area of an exit of the composition outlet to the total cross-sectional area of air outlets is between 16:1 and 1:1.

16. The inhaler according to claim 15, wherein the ratio of cross-sectional area of the exit of the composition outlet to the total cross-sectional area of air outlets is between 4:1 and 1:1.

17. An inhaler according to claim 1, wherein the total cross sectional exit area of the composition outlet is 0.008 $mm^2$ to 0.8 $mm^2$ and the total cross-sectional area of air outlets is from 0.14 $mm^2$ to 1.0 $mm^2$ wherein the ratio of the two areas is 2:1 to 8:1, and gives a droplet size of 5 microns as a D50.

18. The inhaler of claim 17 wherein the total cross-sectional exit area of the composition outlet is 0.07 $mm^2$ to 0.2 $mm^2$ and gives a droplet size of 0.6 microns.

19. An inhaler according to claim 1, wherein the pressure drop across the air outlets as measured with twin air jets is 0.5-4 kPa.

20. An inhaler according to claim 19, where the pressure drop as measured with twin air jets is 2-4 kPa.

* * * * *